(12) United States Patent
Okita et al.

(10) Patent No.: US 11,174,972 B2
(45) Date of Patent: Nov. 16, 2021

(54) PIPE JOINT (71) Applicant: SMC Corporation, Chiyoda-ku (JP)

(72) Inventors: Yuzuru Okita, Tsukubamirai (JP); Keisuke Ikeda, Abiko (JP)

(73) Assignee: SMC Corporation, Chiyoda-ku (JP)

( * ) Notice: Subject to any disclaimer, the term of this patent is extended or adjusted under 35 U.S.C. 154(b) by 0 days.

(21) Appl. No.: 16/749,233

(22) Filed: Jan. 22, 2020

(65) Prior Publication Data
US 2020/0158272 A1 May 21, 2020

Related U.S. Application Data (62) Division of application No. 14/705,031, filed on May 6, 2015.

(30) Foreign Application Priority Data

Jul. 7, 2014 (JP) .................. 2014-139354

(51) Int. Cl.
*F16L 19/04* (2006.01)
*F16L 33/22* (2006.01)
(Continued)

(52) U.S. Cl.
CPC .......... *F16L 33/245* (2013.01); *A61M 39/10* (2013.01); *A61M 39/12* (2013.01); *F16L 33/223* (2013.01); *A61M 2039/1033* (2013.01)

(58) Field of Classification Search
CPC ... F16L 19/005; F16L 19/0283; F16L 19/043; F16L 19/046; F16L 19/06; F16L 33/223;
(Continued)

(56) References Cited

U.S. PATENT DOCUMENTS 768,188 A 8/1904 Reeve
1,195,433 A 8/1916 Bailey
(Continued)

FOREIGN PATENT DOCUMENTS

GB 869241 A 5/1961
JP 06159574 A 6/1994
(Continued)

OTHER PUBLICATIONS

Japanese Office Action dated Jun. 2, 2015 in Patent Application No. 2014-139354 (with Partial English Translation).
(Continued)

*Primary Examiner* — Amber R Anderson
*Assistant Examiner* — Stacy N Lawson
(74) *Attorney, Agent, or Firm* — Oblon, McClelland, Maier & Neustadt, L.L.P.

(57) ABSTRACT

A pipe joint includes a joint body formed with a through hole therein along an axial direction, and having male threads and an extending shaft portion formed on one end side thereof; and a nut member formed with an insertion hole through which a tube member is inserted, and having female threads formed therein that screw-engage with the male threads. Annular projections are formed on an outer circumferential surface of the extending shaft portion, and the tube member, which is expanded in diameter, is gripped between the annular projections and an inner circumferential surface of the nut member.

5 Claims, 9 Drawing Sheets

(51) Int. Cl.
*F16L 47/04* (2006.01)
*F16L 33/24* (2006.01)
*A61M 39/12* (2006.01)
*A61M 39/10* (2006.01)

(58) Field of Classification Search
CPC ...... F16L 33/245; A61M 39/10; A61M 39/12; A61M 2039/1033
USPC ................................ 285/247, 354, 386, 389
See application file for complete search history.

(56) References Cited

U.S. PATENT DOCUMENTS

| | | | |
|---|---|---|---|
| 1,233,401 A | | 7/1917 | McIntyre |
| 2,551,536 A | * | 5/1951 | Harvey ............... F16L 33/223 |
| | | | 285/148.13 |
| 2,782,059 A | | 2/1957 | Stranberg |
| 4,736,969 A | | 4/1988 | Fouts |
| 4,887,847 A | | 12/1989 | Barnoach |
| 4,951,976 A | | 8/1990 | Boelkins |
| 5,622,393 A | | 4/1997 | Elbich |
| 5,794,986 A | | 8/1998 | Gansel |
| 2004/0100097 A1 | | 5/2004 | Fukano |
| 2004/0245776 A1 | | 12/2004 | Evans |
| 2011/0221190 A1 | * | 9/2011 | Teshima ............... F16L 19/041 |
| | | | 285/354 |
| 2011/0260450 A1 | * | 10/2011 | Imanishi ............... F16L 35/00 |
| | | | 285/334.5 |
| 2014/0353965 A1 | | 12/2014 | Inoue et al. |

FOREIGN PATENT DOCUMENTS

| | | |
|---|---|---|
| JP | 11-230463 A | 8/1999 |
| JP | 2000-230684 A | 8/2000 |
| JP | 3251196 | 1/2002 |
| JP | 2011-12691 A | 1/2011 |
| JP | 2011012691 A | 1/2011 |
| JP | 10-1275763 B1 | 6/2013 |
| JP | 2014-31878 A | 2/2014 |

OTHER PUBLICATIONS

Office Action dated Mar. 4, 2016 in Korean Patent Application No. 10-2015-0083306 with partial English translation.

* cited by examiner

PIPE JOINT

CROSS-REFERENCE TO RELATED APPLICATION

This application is a Divisional Application of U.S. Ser. No. 14/705,031 filed May 6, 2015, which is based upon and claiming the benefit of priority from prior Japanese Patent Application No. 2014-139354, filed Jul. 7, 2014, the entire contents of each of which are incorporated herein by reference.

BACKGROUND OF THE INVENTION

Field of the Invention

The present invention relates to a pipe joint, which enables a pipe member such as a tube or the like to be connected in a liquid-tight or airtight manner to a fluid device, for thereby facilitating piping for a high purity liquid or ultrapure water that is handled in a production process, such as the production of semiconductor devices, production of medical equipment and medicines, food processing, and processes in the chemical industry.

Description of the Related Art

As a pipe joint of this type, a pipe joint is known in which one end of a tube member is sandwiched and gripped in a gap between a joint main body and a nut member that is threaded or screw-engaged on the joint main body.

For example, in Japanese Patent No. 3251196, a pipe joint is disclosed in which an opening edge of a through hole of the pipe joint is arranged in confronting relation to a back wall of a nut member, and a stepped part, which extends from a general outer diameter portion to an expanded diameter portion of the tube member, is positioned in a gap between the back wall and the opening edge of the through hole. In the pipe joint, as the nut member is screw-advanced, the gap between the back wall and the opening edge of the through hole becomes narrower, and a projecting ridge that is formed on the opening edge portion presses the stepped part of the tube member against the back wall. Consequently, gaps formed mutually between the projecting ridge, the stepped part of the tube member, and the back wall are made to vanish, and sufficiently tight contact therebetween is obtained, while in addition, since the projecting ridge bites into the stepped part of the tube member, coming off or inadvertent removal of the tube member can be prevented.

SUMMARY OF THE INVENTION

However, with the pipe joint of Japanese Patent No. 3251196, if the nut member becomes loosened due to external factors or stress relaxation, the sealing ability decreases, and leakage of fluid tends to occur, along with the concern that the tube member may come off or be inadvertently removed.

The present invention has been devised while taking into consideration the aforementioned problems, and has the object of providing a pipe joint in which, even in the case that a nut member becomes loosened due to external factors or stress relaxation, the sealing ability is reliably maintained, and coming off or inadvertent removal of the tube is reliably prevented.

The pipe joint according to the present invention includes a joint body formed with a through hole therein along an axial direction, and having male threads and an extending shaft portion formed on one end side thereof, and a nut member formed with an insertion hole through which a tube member is inserted, and having female threads formed therein that screw-engage with the male threads. Annular projections are formed on an outer circumferential surface of the extending shaft portion, and the tube member, which is expanded in diameter, is gripped between the annular projections and an inner circumferential surface of the nut member.

With the above-described pipe joint, since the pipe member is gripped between the annular projections and the inner circumferential surface of the nut member, even in the case that through prolonged usage loosening of the nut member takes place, the seal between distal ends of the annular projections and the inner circumferential surface of the tube member, as well as the holding force of the tube member are maintained, and thus, a stable sealing ability is exhibited, and coming off or inadvertent removal of the tube member is reliably prevented.

In the aforementioned pipe joint, a first tapered surface may be formed on an end of the extending shaft portion, an annular latching part may be formed on an edge of an opening of the insertion hole proximate the first tapered surface, an inner wall surface of the expanded diameter tube member may be pressed against the first tapered surface, and the annular latching part of the nut member may be placed in abutment against an outer wall surface of the expanded diameter tube member. According to this feature, since the tube member is gripped between the first tapered surface of the extending shaft portion and the annular latching part of the nut member, the sealing ability is further improved, and coming off of the tube member can be prevented more reliably.

Further, a second tapered surface, which flares outward in a direction toward the male threads, may be formed on an end of the extending shaft portion on a side proximate the male threads, and a third tapered surface may be formed on an inner circumferential surface of the nut member at a position facing the second tapered surface. In this case, the expanded diameter tube member is sandwiched between the second tapered surface and the third tapered surface. According to this feature, since the tube member is sandwiched between the second tapered surface of the extending shaft portion and the third tapered surface of the nut member, coming off of the tube member is reliably prevented.

Furthermore, projections, which regulate an amount of tightening of the nut member with respect to the joint body, preferably are formed on an end surface of the nut member. According to this feature, overtightening of the nut member is prevented.

Plural arcuately shaped grooves preferably are formed on the joint body in confronting relation to the projections, the plural arcuately shaped grooves having widths that allow insertion of the projections therein, and the projections and the plural arcuately shaped grooves preferably are disposed on a common circumference as viewed in the axial direction. According to this feature of the invention, a worker who uses the pipe joint can easily be notified that the nut member has been tightened appropriately.

Further, nut side annular projections may be formed on the inner circumferential surface of the nut member, such that the nut side annular projections press against the expanded diameter tube member in directions toward recesses that are formed between adjacent ones of the annular projections. According to this feature, since the tube member is gripped between the nut side annular projections and the annular projections that are formed on the extending shaft portion, the sealing ability and holding force are further enhanced. In addition, since the nut side annular projections and the annular projections that are formed on the extending shaft portion are disposed alternately, deformation of the tube member can be performed smoothly.

Moreover, nut side annular projections may be formed on the inner circumferential surface of the nut member, such that the nut side annular projections press against the expanded diameter tube member in directions toward the annular projections. According to this feature, since the tube member is gripped between the nut side annular projections and the annular projections that are formed on the extending shaft portion, the sealing ability and holding force are further enhanced. In addition, since the nut side annular projections and the annular projections that are formed on the extending shaft portion are disposed in confronting relation to each other, the force with which the tube member is gripped is further increased.

In accordance with the pipe joint of the present invention, even in the case that the nut member becomes loosened due to external factors or stress relaxation, a stable sealing ability is exhibited, and coming off or inadvertent removal of the tube member is reliably prevented.

The above and other objects, features and advantages of the present invention will become more apparent from the following description when taken in conjunction with the accompanying drawings, in which preferred embodiments of the present invention are shown by way of illustrative example.

DESCRIPTION OF THE PREFERRED EMBODIMENT

Preferred embodiments of pipe joints according to the present invention will be described in detail below with reference to the accompanying drawings.

Figure 1:
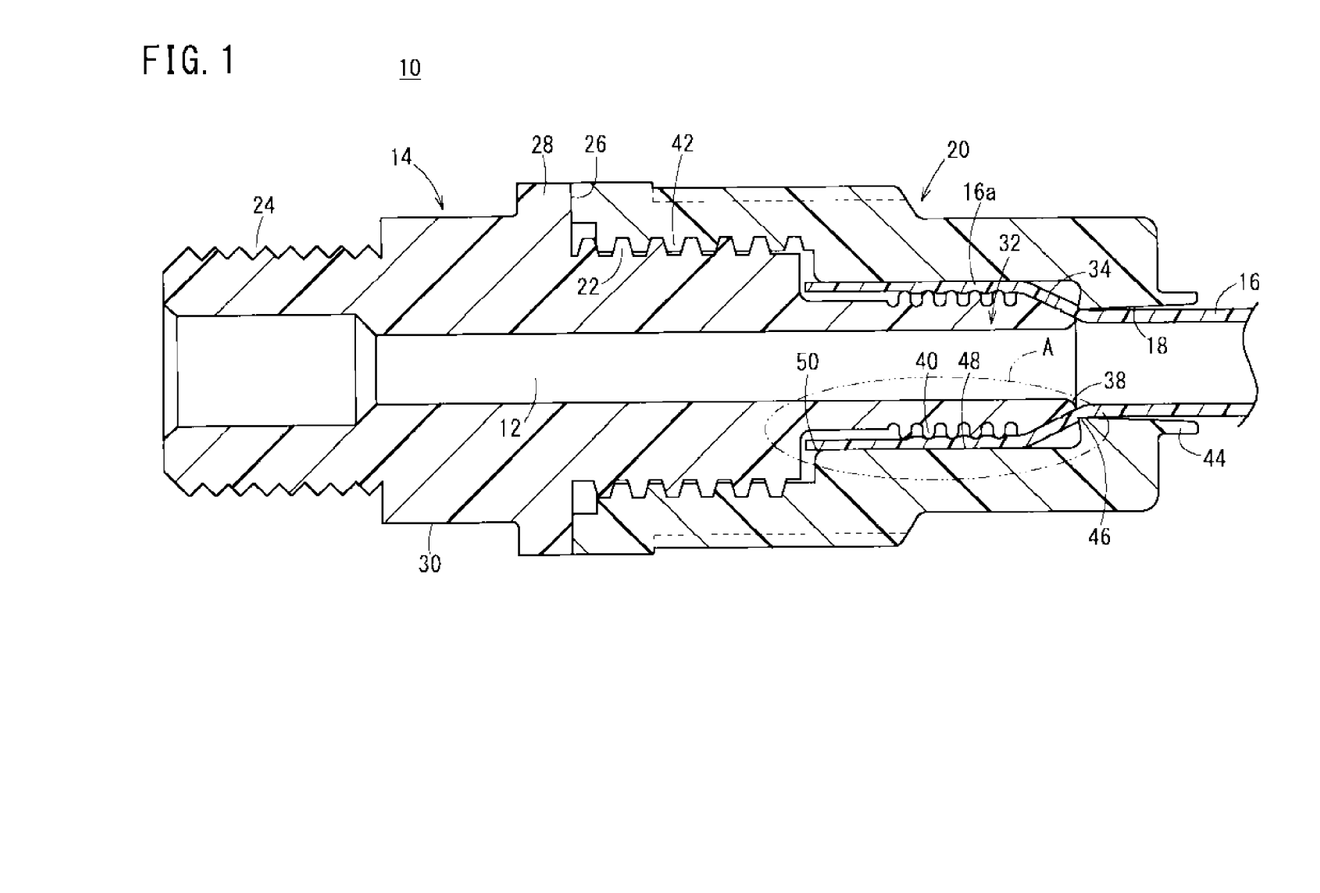
FIG. 1 is a longitudinal cross sectional view along an axial direction of a pipe joint according to a first embodiment of the present invention.
Figure 2:
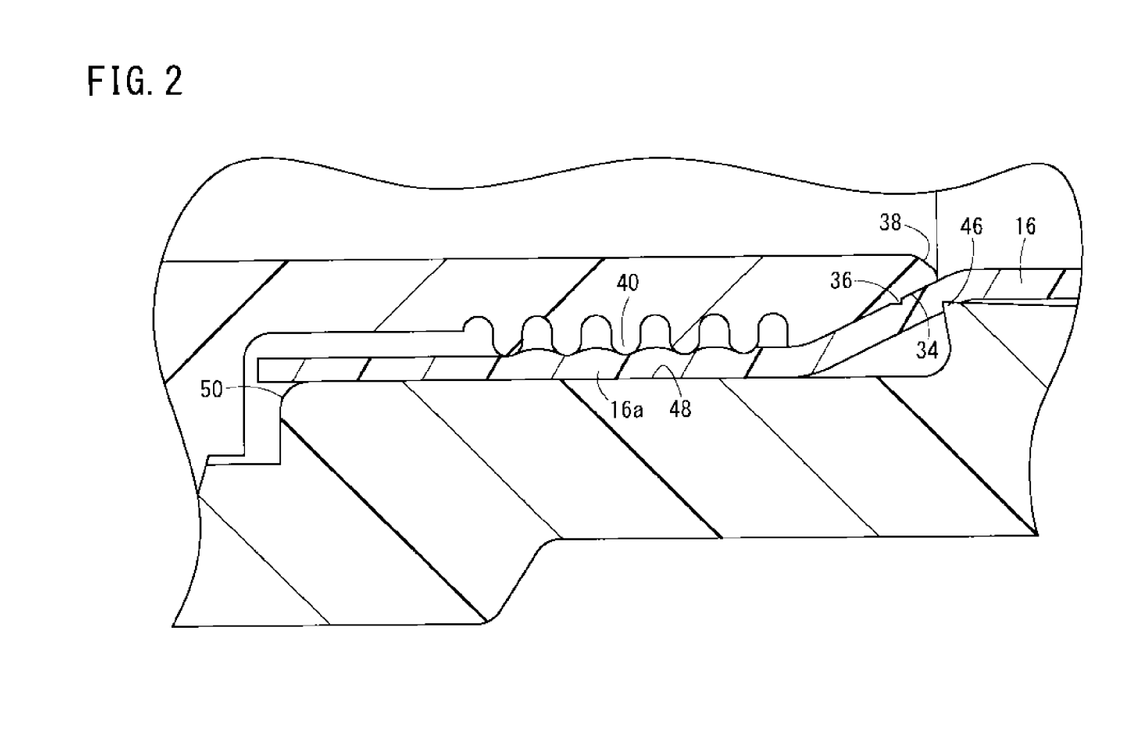
FIG. 2 is an enlarged longitudinal cross sectional view of a portion A of the pipe joint shown in FIG. 1.
Figure 3:
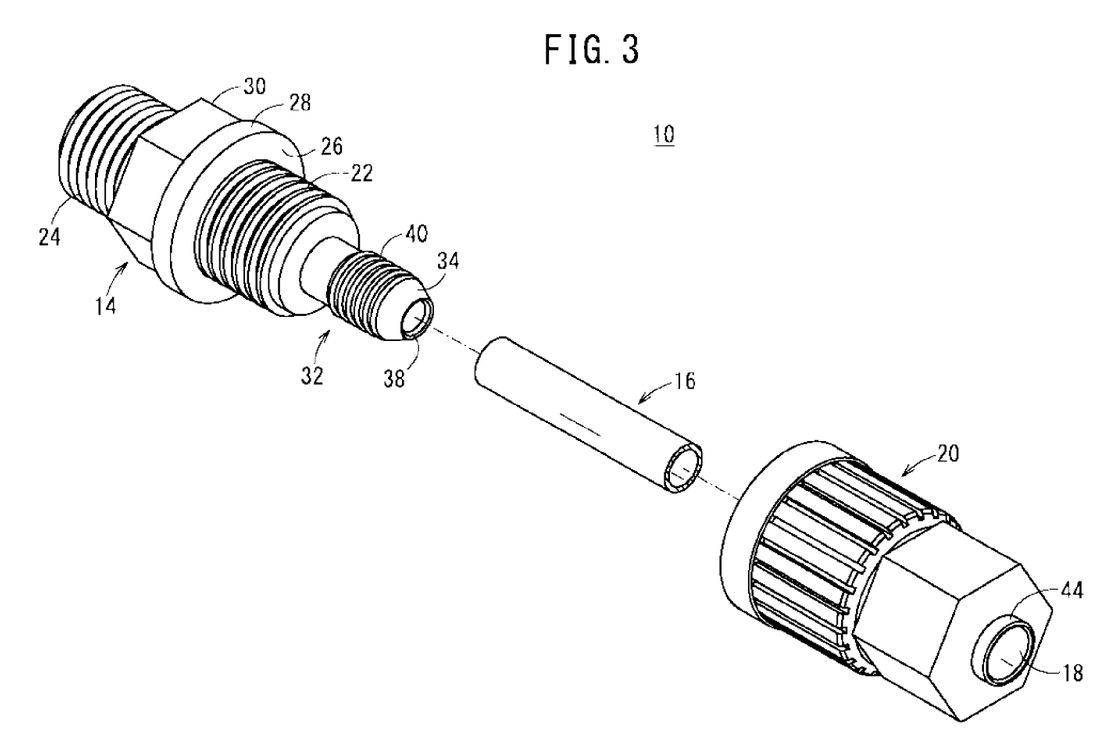
FIG. 3 is a partial exploded perspective view of the pipe joint shown in FIG. 1.

A pipe joint 10 according to a first embodiment will be described with reference to FIGS. 1 through 3.

The pipe joint 10 includes a substantially cylindrical joint body 14 having a through hole 12 therein that functions as a fluid passage and is formed in a straight line along an axial direction, and an insertion hole 18 having a circular shape in cross section and into which a tube (tube member) 16 is inserted. In addition, the pipe joint 10 is equipped with a nut member 20 that retains the tube 16 by being fitted onto the joint body 14. Any of the joint body 14, the nut member 20, and the tube 16 may be formed from a fluorine resin.

On the joint body 14, there are provided a first male threaded portion 22 with threads, which are substantially trapezoidal in cross section, formed on an outer circumferential surface in the vicinity of one end of the joint body 14, and a second male threaded portion 24 with threads, which are of a serrated shape in cross section, formed on the outer circumferential surface on another end of the joint body 14. At a terminal end of the first male threaded portion 22 proximate the second male threaded portion 24, an annular projection 28 is formed that bulges in a radial outward direction via an annular stepped part 26 made up from a planar surface that circles around the joint body 14, and further, a polygonal part 30 is formed between the annular projection 28 and the second male threaded portion 24. The polygonal part 30 is hexagonal in cross section, for enabling a tool such as a non-illustrated spanner and the like to grip the joint body 14.

On the one end of the joint body 14, a small diameter extending shaft portion 32 is formed. The small diameter extending shaft portion 32 has the through hole 12 therein that extends in the axial direction, and enables an expanded diameter portion 16a of the tube 16 to be inserted thereover. A first tapered surface 34, which expands gradually in diameter in the direction in which the tube 16 is inserted, is provided on the end of the extending shaft portion 32. A small annular projection 36, which is in the shape of a chevron in cross section, is formed on the first tapered surface 34 to project from the first tapered surface 34 (see FIG. 2). At a border region between the first tapered surface 34 and the through hole 12, a first chamfered part 38 is formed for suppressing the occurrence of liquid pooling.

Plural annular projections 40, which abut against an inner wall surface of the expanded diameter portion 16a of the tube 16, are provided on an outer circumferential surface of the extending shaft portion 32 contiguous with the first tapered surface 34. The cross section of the circumference of the plural annular projections 40 is semicircle. The plural annular projections 40 are juxtaposed along the axial direction with predetermined intervals formed mutually therebetween. In the example shown in FIG. 2, five of such annular projections are provided. The heights of the annular projections 40 are substantially uniform. Moreover, the annular projections 40 need not necessarily be disposed in a plurality, and only one of such annular projections 40 may be provided.

A female threaded portion 42, which can be screw-engaged with the first male threaded portion 22 of the joint body 14, is formed on an inner circumferential surface of the nut member 20. An annular projection 44 is formed on an exterior side of the nut member 20 adjacent to the insertion hole 18. The projection 44 carries out a function to protect the tube 16, by preventing breakage or kinking of the tube 16 that projects outwardly from the insertion hole 18. If the distal end of the projection 44 is expanded outward in diameter, an advantage is obtained in that insertion of the tube 16 is made easier.

An annular latching part 46, which is shaped as an acute angle in cross section, is formed on an inner side of the nut member 20 adjacent to the insertion hole 18. The annular latching part 46 carries out a function to engage with the inclined outer circumferential surface of the tube 16, and to press the tube 16 toward the first tapered surface 34 of the joint body 14 at the time that the nut member 20 is tightened with respect to the joint body 14.

On an inner circumferential surface of the nut member 20 between the annular latching part 46 and the female threaded portion 42, an annular pressing part 48 is formed, which is pressed in abutment against an outer wall surface of the expanded diameter portion 16*a* of the tube 16. The annular pressing part 48 has a cylindrical surface having a substantially uniform inner diameter. A second chamfered part 50, which is chamfered with a predetermined radius of curvature, is formed on an end of the annular pressing part 48 near the female threaded portion 42. A predetermined gap or clearance is formed between the annular pressing part 48 and each of the annular projections 40 of the extending shaft portion 32 of the joint body 14. The distances between each end of the annular projections 40 and the annular pressing part 48 are substantially equivalent to each other, such that as described later, at a time that the expanded diameter portion 16*a* of the tube 16 is formed, the distance between the annular projections 40 and the annular pressing part 48 is less than the thickness of the expanded diameter portion 16*a*.

Consequently, by tightening the nut member 20 onto the joint body 14, the expanded diameter portion 16*a* of the tube 16 is sandwiched and gripped between the plural annular projections 40 and the annular pressing part 48. As a result, the inner wall surface of the expanded diameter portion 16*a* is held in tight contact with the plural annular projections 40, and a first seal is formed between the distal ends of each of the annular projections 40 and the inner wall surface of the expanded diameter portion 16*a*.

By increasing the amount by which the nut member 20 is tightened with respect to the joint body 14, the tube 16 is gripped between the annular latching part 46 of the nut member 20 and the first tapered surface 34 of the extending shaft portion 32 of the joint body 14. As a result, the first tapered surface 34 of the extending shaft portion 32 is held in tight contact with the slanted inner wall surface of the tube 16 by means of the annular latching part 46, and a second seal is formed between the first tapered surface 34 of the extending shaft portion 32 and the slanted inner wall surface of the tube 16.

The pipe joint 10 according to the present embodiment is constructed basically as described above. Next, operations and advantages of the pipe joint 10 will be described.

Initially, the tube 16 is inserted along the insertion hole 18 of the nut member 20, such that the end of the tube 16 is positioned up to a predetermined length on the inner side of the nut member 20.

Next, the extending shaft portion 32 of the joint body 14 is inserted into the nut member 20 from the female threaded portion 42's side, and the female threaded portion 42 of the nut member 20 is screw-rotated and threaded along the first male threaded portion 22 of the joint body 14.

As the nut member 20 is tightened, the tube 16 undergoes expansion in diameter in order from the distal end side thereof along the first tapered surface 34 of the extending shaft portion 32. Further, the annular pressing part 48 of the nut member 20 and the extending shaft portion 32 of the joint body 14 gradually come to overlap one another in the axial direction, whereupon, among the plural annular projections 40 of the extending shaft portion 32, the annular projections 40 are placed in confronting relation to the annular pressing part 48, in order from the side that is nearest to the first tapered surface 34. The annular pressing part 48, which faces the annular projections 40, presses the expanded diameter outer wall surface of the tube 16 toward the annular projections 40. More specifically, after being expanded in diameter, the tube 16 is deformed while being squeezed in order from the side nearest to the first tapered surface 34, and the inner wall of the expanded diameter portion 16*a* is compressed at regions thereof that are in contact with the respective annular projections 40, whereas on both sides of such regions, the inner wall expands diametrically inward and becomes inserted into spaces between the adjacent annular projections 40.

When carried out in this manner, the expanded diameter portion 16*a* of the tube 16 is formed, together with the expanded diameter portion 16*a* being gripped between the plural annular projections 40 of the extending shaft portion 32 and the annular pressing part 48 of the nut member 20. Consequently, a seal, i.e. the first seal, is accomplished between the distal ends of the plural annular projections 40 and the inner wall surface of the tube 16.

Upon the nut member 20 being further tightened, when the distal end of the nut member 20 comes into abutment against the annular stepped part 26 of the joint body 14, the annular latching part 46 of the nut member 20 engages with the inclined outer circumferential surface of the tube 16 and presses the tube 16 toward the first tapered surface 34 of the joint body 14. As a result, the tube 16 is gripped between the first tapered surface 34 of the extending shaft portion 32 and the annular latching part 46 of the nut member 20, and a seal, i.e., the second seal, is accomplished between the first tapered surface 34 of the extending shaft portion 32 and the slanted inner wall surface of the tube 16.

Consequently, when tightening of the nut member 20 is completed, since seals are established by both the first seal and the second seal, a strong sealing ability can be realized.

Further, even in the case that a force to pull out the tube 16 is applied thereto in a direction opposite to the direction in which the tube 16 was inserted, because the tube 16 is gripped between the annular pressing part 48 of the nut member 20 and the respective annular projections 40 of the extending shaft portion 32 of the joint tube 14, and also is gripped between the annular latching part 46 of the nut member 20 and the first tapered surface 34 of the extending shaft portion 32 of the joint body 14, pulling out of the tube 16 from the joint body 14 can reliably be prevented. Moreover, by biting into the inner wall surface of the tube 16, the small annular projection 36 that is formed on the first tapered surface 34 performs an action to prevent coming off or inadvertent removal of the tube 16.

In this regard, even in the case that due to prolonged usage over an extended period the tightening force becomes reduced, and loosening of the nut member 20 with respect to the joint body 14 occurs, the respective annular projections 40 of the extending shaft portion 32 of the joint body 14 are maintained in confronting relation at a predetermined distance to the annular pressing part 48 of the nut member 20. More specifically, since a condition is maintained in which the expanded diameter portion 16*a* of the tube 16 is gripped between the annular pressing part 48 and the plural annular projections 40, at least the sealing force at the first seal is maintained, and a stable sealing ability can be exhibited continuously. Further, the force that acts to hold the tube 16 between the respective annular projections 40 and the annular pressing part 48 is maintained, so there is no risk of the tube 16 coming out from the joint body 14.

Figure 4:
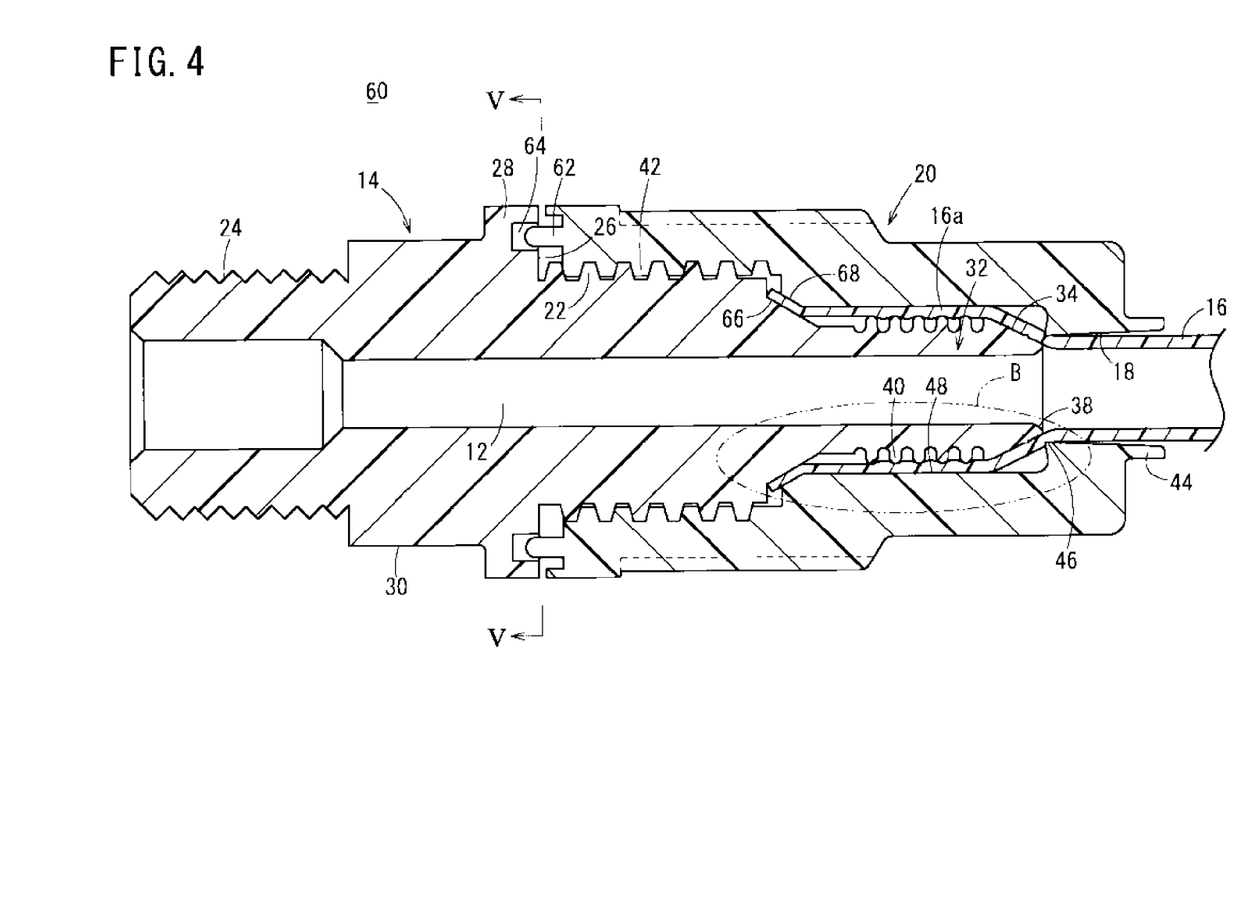
FIG. 4 is a longitudinal cross sectional view along an axial direction of a pipe joint according to a second embodiment of the present invention.
Figure 5:
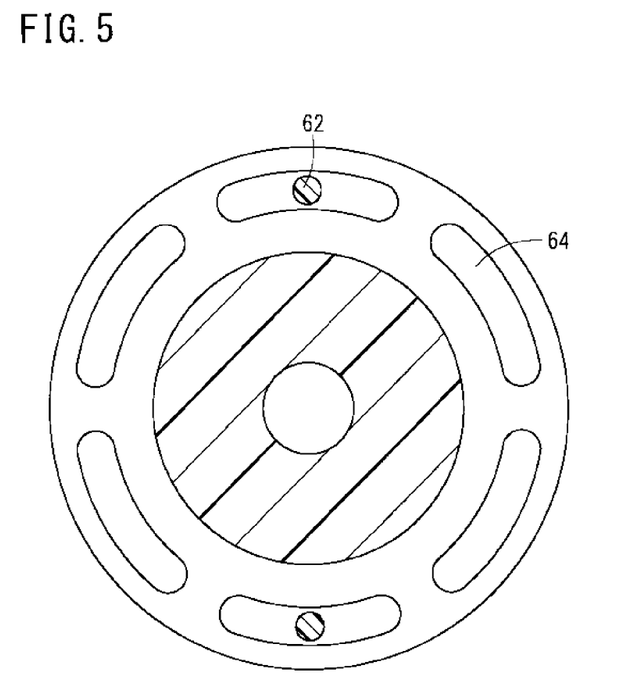
FIG. 5 is a cross sectional view taken along line V-V of the pipe joint shown in FIG. 4.
Figure 6:
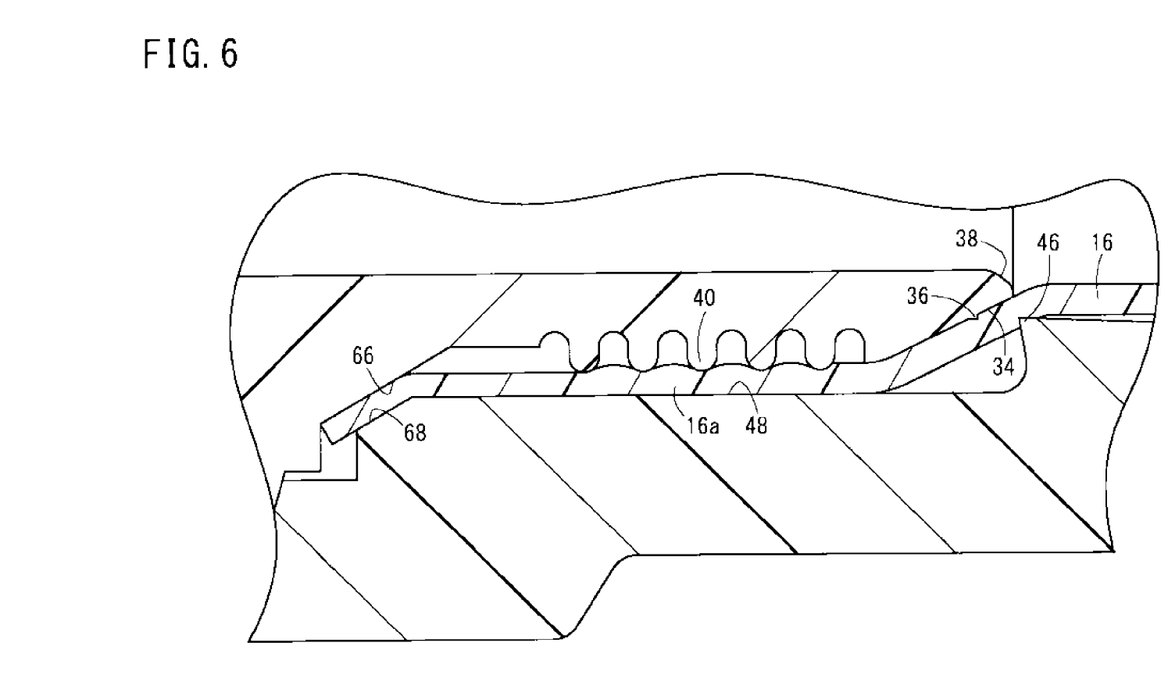
FIG. 6 is an enlarged longitudinal cross sectional view of a portion B of the pipe joint shown in FIG. 4.

A pipe joint 60 according to a second embodiment will be described with reference to FIGS. 4 through 6. Constituent elements which are the same as those of the pipe joint 10 according to the first embodiment are denoted by the same reference characters, and detailed description of such features is omitted.

The pipe joint 60 according to the second embodiment differs from the pipe joint 10 according to the first embodiment, in that the pipe joint 60 is equipped with means for regulating the amount of tightening of the nut member 20, together with informing a worker who uses the pipe joint 60 that a predetermined amount of tightening has been reached. In addition, the pipe joint 60 is equipped with means for further gripping the tube 16 on a distal end of the expanded diameter portion 16a.

On an end face of the nut member 20 on the side of the female threaded portion 42, plural cylindrical post-shaped end face projections 62 are formed integrally. The end face projections 62 project out a predetermined length from the end face of the nut member 20. On the other hand, on an annular projection 28 of the joint body 14, plural arcuately shaped grooves 64 are provided that open on the annular stepped part 26. The plural arcuately shaped grooves 64 are of the same shape mutually, having a width that is wider than the diameter of each of the end face projections 62, and are evenly arranged on the same circumference around the axis of the joint body 14. As viewed along the axial direction, the respective end face projections 62 are positioned on the same circumference as the circumference on which the plural arcuately shaped grooves 64 are arranged. In the illustrated example, two end face projections 62 are formed on diametrically opposite sides, whereas six arcuately shaped grooves 64 are formed, each having a length, respectively, corresponding to a central angle of approximately 45 degrees. Moreover, the end face projections 62 need not necessarily be disposed in a plurality, and only one of such end face projections 62 may be provided.

On an end of the extending shaft portion 32 on a side proximate the first male threaded portion 22 of the joint body 14, a second tapered surface 66 is formed, which flares outward in a direction toward the first male threaded portion 22. A third tapered surface 68, which flares outward in a direction toward the female threaded portion 42, is formed between the female threaded portion 42 and the annular pressing part 48 of the nut member 20. The second tapered surface 66 of the joint body 14 and the third tapered surface 68 of the nut member 20 have substantially the same angle of inclination, such that when the nut member 20 is tightened onto the joint body 14, both tapered surfaces are opposed to each other across a predetermined gap.

The pipe joint 60 according to the present embodiment is constructed basically as described above. Next, operations and advantages of the pipe joint 60 will be described.

First, the tube 16 is inserted along the insertion hole 18 of the nut member 20, and then, the extending shaft portion 32 of the joint body 14 is inserted on the side of the female threaded portion 42 of the nut member 20, and the female threaded portion 42 of the nut member 20 is screw-rotated and threaded along the first male threaded portion 22 of the joint body 14.

As the nut member 20 is tightened, the tube 16 undergoes expansion in diameter in order from the distal end side thereof, and the annular pressing part 48 of the nut member 20 and the extending shaft portion 32 of the joint body 14 come to overlap one another in the axial direction. Consequently, the expanded diameter portion 16a of the tube 16 is gripped between the respective annular projections 40 of the extending shaft portion 32 of the joint body 14 and the annular pressing part 48 of the nut member 20.

As the nut member 20 is further tightened, the respective end face projections 62 formed on the end face of the nut member 20 move to approach the annular stepped part 26. In addition, accompanying threaded advancement of the nut member 20, after the respective end face projections 62 surpass the planar surface of the stepped part 26, and have entered into respective ones of the arcuately shaped grooves 64, as viewed along the axial direction, when the respective end face projections 62 arrive at positions where they are about to separate away from the respective arcuately shaped grooves 64, the respective end face projections 62 collide against the inner side walls of the respective arcuately shaped grooves 64. Therefore, further tightening of the nut member 20 beyond this position is regulated, and by the sound and a feeling of resistance when the end face projections 62 collide against the inner side surfaces of the arcuately shaped grooves 64, the worker is notified that tightening of the nut member 20 has reached a predetermined amount, or stated otherwise, that the nut member 20 has been tightened appropriately.

Substantially at the same time as the respective end face projections 62 collide against the inner side surfaces of the respective arcuately shaped grooves 64 or at a timing slightly before this collision takes place, the annular latching part 46 of the nut member 20 engages with the inclined outer circumferential surface of the tube 16, whereupon the tube 16 is pressed toward the side of the first tapered surface 34 of the joint body 14. Further, the distal end side of the expanded diameter portion 16a of the tube 16 is gripped between the second tapered surface 66 of the joint body 14 and the third tapered surface 68 of the nut member 20.

When tightening of the nut member 20 has been performed appropriately, the tube 16 becomes gripped respectively between the respective annular projections 40 of the extending shaft portion 32 of the joint body 14 and the annular pressing part 48 of the nut member 20, between the first tapered surface 34 of the extending shaft portion 32 of the joint body 14 and the annular latching part 46 of the nut member 20, and between the second tapered surface 66 of the joint body 14 and the third tapered surface 68 of the nut member 20. In this manner, even if a force to pull out the tube 16 is applied in a direction opposite to the direction in which the tube 16 was inserted, pulling out of the tube 16 from the joint body 14 can reliably be prevented.

Figure 7:
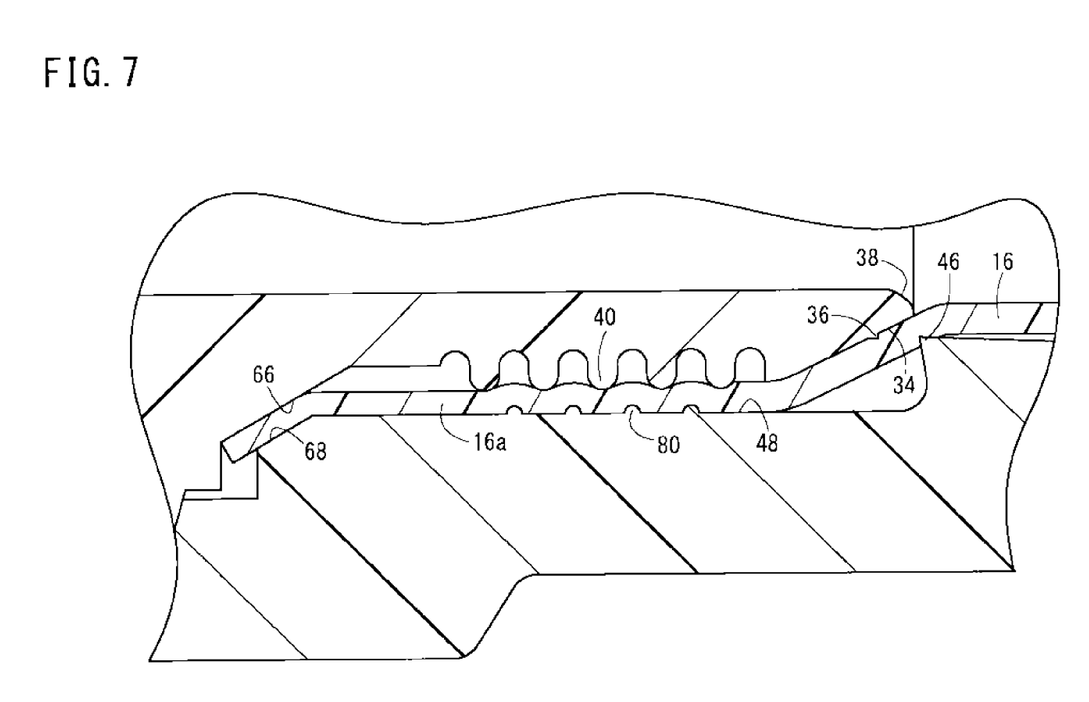
FIG. 7 is a partially enlarged longitudinal cross sectional view of a pipe joint according to a third embodiment of the present invention.

A pipe joint 10 according to a third embodiment will be described with reference to FIG. 7. The pipe joint according to the present embodiment differs from the pipe joint 60 according to the second embodiment only in relation to a part of the structure of the annular pressing part 48 of the nut member 20. FIG. 7 is a view corresponding to the partially enlarged longitudinal cross sectional view of the pipe joint 60 according to the second embodiment shown in FIG. 6.

On the annular pressing part 48 of the nut member 20, plural nut side annular projections 80 are formed, which abut against the outer wall surface of the expanded diameter portion 16a of the tube 16. The nut side annular projections 80 have substantially the same height with semicircular shapes in cross section, and are laid out along the axial direction with predetermined intervals formed mutually therebetween. The nut side annular projections 80 are smaller than the annular projections 40 that are formed on the extending shaft portion 32 of the joint body 14. When the nut member 20 is tightened onto the joint body 14, the respective nut side annular projections 80 are disposed at a middle position between one annular projection 40 formed on the extending shaft portion 32 and another annular projection 40 that lies adjacent thereto.

When the expanded diameter portion 16a of the tube 16 is inserted over the extending shaft portion 32 of the joint body 14, and the nut member 20, which is fitted loosely over the tube 16, is tightened, the expanded diameter portion 16a of the tube 16 is gripped between the plural annular projections 40, which are formed on the extending shaft portion 32, and the plural nut side annular projections 80, which are formed on the annular pressing part 48. Therefore, the sealing ability between the plural annular projections 40 and the inner wall surface of the tube 16 is further enhanced, and the force with which the tube 16 is held is further improved.

Further, because the plural annular projections 40 and the plural nut side annular projections 80 are arranged alternately, the expanded diameter portion 16a of the tube 16 bulges radially inward on both sides of each of the annular projections 40 while being pressed by the nut side annular projections 80, and is deformed so as to enter into the spaces between the adjacent annular projections 40. Therefore, the expanded diameter portion 16a of the tube 16 is deformed easily in a wave-like shape.

Figure 8:
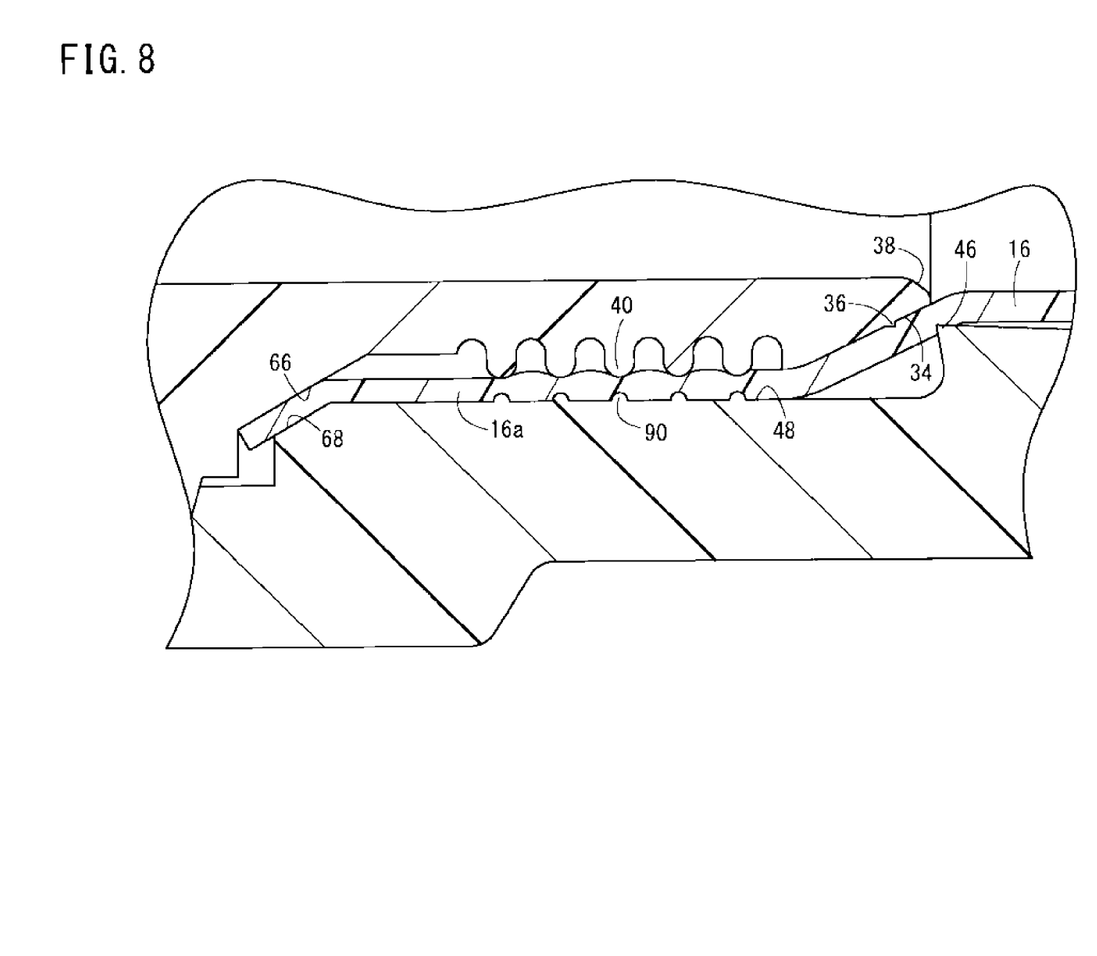
FIG. 8 is a partially enlarged longitudinal cross sectional view of a pipe joint according to a fourth embodiment of the present invention.

Next, a pipe joint according to a fourth embodiment will be described with reference to FIG. 8. The pipe joint according to the present embodiment differs from the pipe joint 60 according to the second embodiment and from the pipe joint according to the third embodiment only in relation to a part of the structure of the annular pressing part 48 of the nut member 20. FIG. 8 is a view corresponding to the partially enlarged longitudinal cross sectional view of the pipe joint 60 according to the second embodiment shown in FIG. 6.

On the annular pressing part 48 of the nut member 20, the plural nut side annular projections 90 are formed, which abut against the outer wall surface of the expanded diameter portion 16a of the tube 16. The nut side annular projections 90 have substantially the same height with semicircular shapes in cross section, and are laid out along the axial direction with predetermined intervals formed mutually therebetween. The nut side annular projections 90 are smaller than the annular projections 40 that are formed on the extending shaft portion 32 of the joint body 14. When the nut member 20 is tightened onto the joint body 14, the nut side annular projections 90 are disposed at positions each confronting exactly with one of the annular projections 40, respectively, which are formed on the extending shaft portion 32.

When the expanded diameter portion 16a of the tube 16 is inserted over the extending shaft portion 32 of the joint body 14, and the nut member 20, which is fitted loosely over the tube 16, is tightened, the expanded diameter portion 16a of the tube 16 is gripped between the plural annular projections 40, which are formed on the extending shaft portion 32, and the plural nut side annular projections 90, which are formed on the annular pressing part 48. Therefore, the sealing ability between the plural annular projections 40 and the inner wall surface of the expanded diameter portion 16a of the tube 16 is further enhanced, and the force with which the tube 16 is held is further improved.

Further, since the respective annular projections 40 and the respective nut side annular projections 90 are arranged at positions that directly confront one another, the force with which the tube 16 is gripped by the respective annular projections 40 and the respective nut side annular projections 90 is further increased.

Figure 9:
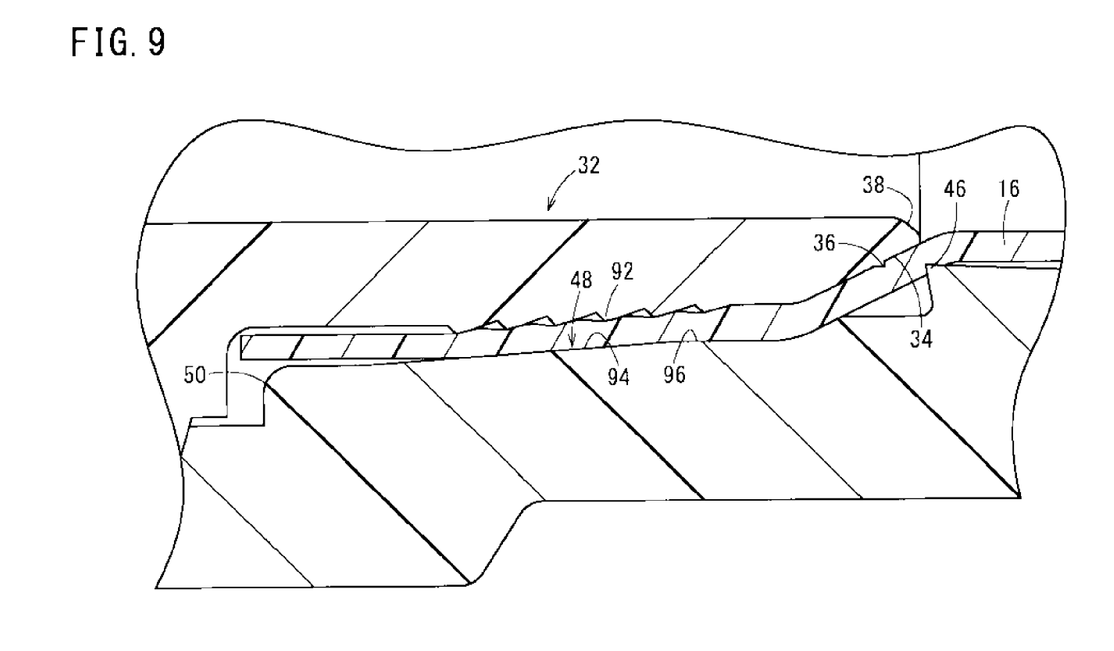
FIG. 9 is a partially enlarged longitudinal cross sectional view of a pipe joint according to a fifth embodiment of the present invention.

Next, a pipe joint according to a fifth embodiment will be described with reference to FIG. 9. The pipe joint according to the present embodiment differs from the pipe joint according to the first embodiment only in relation to parts of the structures of the extending shaft portion 32 of the joint body 14 and the annular pressing part 48 of the nut member 20, respectively. FIG. 9 is a view corresponding to the partially enlarged longitudinal cross sectional view of the pipe joint 10 according to the first embodiment shown in FIG. 2.

Plural annular projections 92, which abut against an inner wall surface of the expanded diameter portion of the tube 16, are formed on an outer circumferential surface of the extending shaft portion 32 contiguous with the first tapered surface 34. Each of the annular projections 92 is chevron shaped in cross section, and includes an inclined surface formed by a gently sloping angle with respect to the axial direction of the extending shaft portion 32, on a side proximate the distal end of the extending shaft portion 32, and further includes an inclined surface, formed by a steeply sloping angle with respect to the axial direction of the extending shaft portion 32, on a side remote from the distal end of the extending shaft portion 32. Owing to this feature, the plural annular projections 92 exhibit a sawtooth shape as a whole. Further, the heights of the plural annular projections 92 become taller as the positions thereof are farther away from the distal end of the extending shaft portion 32.

The annular pressing part 48, which abuts against the outer wall surface of the expanded diameter portion of the tube 16, includes a conical surface 94, which expands in diameter toward the side of the second chamfered part 50, and a cylindrical surface 96 having a uniform inner diameter. In FIG. 9, a line that connects the apexes of the plural annular projections 92 is substantially parallel to the line that defines the conical surface 94. When the nut member 20 is tightened onto the joint body 14, although a majority of the plural annular projections 92 confront the conical surface 94, among the plural annular projections 92, those that are nearest to the distal end of the extending shaft portion 32 confront the cylindrical surface 96.

Since the expanded diameter portion of the tube 16 is gripped between the sawtooth shaped annular projections 92 formed on the extending shaft portion 32 of the joint body 14 and the annular pressing part 48 of the nut member 20, in particular, the force with which the tube 16 is held is enhanced.

The pipe joint according to the present invention is not limited to the embodiment described above. It goes without saying that various alternative or additional configurations may be adopted therein without deviating from the essence of the invention. For example, the nut side annular projections 80, 90 that are formed on the nut member 20 may be modified so as to project in a helical or spiral shape. Further, the expanded diameter portion 16a of the tube 16 may be formed by a separately prepared jig after the tube 16 has been inserted through the insertion hole 18 of the nut member 20, but before the nut member 20 is fitted onto the joint body 14.

What is claimed is:

1. A pipe joint comprising:
a joint body having a through hole therein along an axial direction, and having male threads and an extending shaft portion formed on one end side thereof;
a nut member having an insertion hole through which an elastically deformable tube member is inserted, the nut member having female threads formed therein that screw-engage with the male threads;
radially extending annular projections provided along an annular projection region of an outer circumferential surface of the extending shaft portion, the annular projections having semicircular radially distal ends;

a first tapered surface provided on an axial end of the extending shaft portion;

a tapered-surface-projection projecting outward from the first tapered surface for expanding the elastically deformable tube member inserted in the nut member, wherein the elastically deformable tube member inserted in the nut member includes an expanded diameter portion which is gripped between the annular projections and an inner circumferential surface of the nut member;

a second tapered surface which flares outward in a direction toward the male threads, formed on an end of the extending shaft portion on a side proximate the male threads; and a third tapered surface formed on the inner circumferential surface of the nut member at a position facing the second tapered surface, wherein the expanded diameter portion of the elastically deformable tube member is sandwiched between the second tapered surface and the third tapered surface, wherein the inner circumferential surface of the nut member is cylindrical at least along a length of the nut member corresponding to the annular projection region, and wherein a distance between a radially outermost portion of at least one of said semicircular radially distal ends of the annular projections and the cylindrical inner circumferential surface of the nut member is smaller than a thickness of a portion of the elastically deformable tube member corresponding to a location along the axial direction of at least one of said annular projections prior to the elastically deformable tube member being inserted in the nut member, when the elastically deformable tube member is inserted in the nut member and the female threads are screw-engaged with the male threads, such that the expanded diameter portion of the elastically deformable tube member that is gripped between the annular projections and the inner circumferential surface of the nut member is elastically deformed by the at least one annular projection and a first seal is formed by the radially distal end of said one of said annular projections and an inner wall surface of the expanded diameter portion, wherein end face projections which regulate an amount of tightening of the nut member with respect to the joint body are formed on an end surface of the nut member;

wherein plural arcuately shaped grooves are formed on the joint body in confronting relation to the end face projections;

the plural arcuately shaped grooves have widths that allow insertion of the end face projections therein and have lengths that allow movement of the end face projections in a circumferential direction; and wherein the end face projections and the plural arcuately shaped grooves are disposed on a common circumference as viewed in the axial direction when the female threads are screw-engaged with the male threads.

2. The pipe joint according to claim 1, wherein:

an annular latching part is provided on an edge of an opening of the insertion hole proximate the first tapered surface;

the inner wall surface of the expanded diameter portion of the tube member inserted in the nut member is pressed against the first tapered surface; and the annular latching part abuts against an outer wall surface of the expanded diameter portion of the tube member.

3. The pipe joint according to claim 1, further comprising nut side annular projections formed on the inner circumferential surface of the nut member, wherein:

the nut side annular projections press against the expanded diameter portion of the elastically deformable tube member in directions toward recesses that are formed between adjacent ones of the annular projections.

4. The pipe joint according to claim 1, wherein further comprising nut side annular projections formed on the inner circumferential surface of the nut member:

the nut side annular projections press against the expanded diameter portion of the elastically deformable tube member in directions toward the annular projections.

5. The pipe joint according to claim 1, wherein:

an annular latching part projects from an inner side of the nut member adjacent to the insertion hole, and a second seal is formed at least between the annular latching part and the tapered-surface-projection.

\* \* \* \* \*

UNITED STATES PATENT AND TRADEMARK OFFICE
CERTIFICATE OF CORRECTION

PATENT NO. : 11,174,972 B2
APPLICATION NO. : 16/749233
DATED : November 16, 2021
INVENTOR(S) : Yuzuru Okita et al.

It is certified that error appears in the above-identified patent and that said Letters Patent is hereby corrected as shown below:

In the Claims

Claim 4, Column 12, Lines 1 to 3, change " ...wherein further comprising nut side annular projections formed on the inner circumferential surface of the nut member:" to --...further comprising nut side annular projections formed on the inner circumferential surface of the nut member, wherein:--.

Signed and Sealed this
Twenty-first Day of June, 2022

Katherine Kelly Vidal
*Director of the United States Patent and Trademark Office*